(12) United States Patent
Sato

(10) Patent No.: US 11,208,686 B2
(45) Date of Patent: Dec. 28, 2021

(54) REAGENT FOR EXTRACTING AND AMPLIFYING NUCLEIC ACID

(71) Applicant: TOSOH CORPORATION, Yamaguchi (JP)

(72) Inventor: Hiroshi Sato, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 264 days.

(21) Appl. No.: 16/493,173

(22) PCT Filed: Mar. 7, 2018

(86) PCT No.: PCT/JP2018/008739
§ 371 (c)(1),
(2) Date: Sep. 11, 2019

(87) PCT Pub. No.: WO2018/168600
PCT Pub. Date: Sep. 20, 2018

(65) Prior Publication Data
US 2020/0140924 A1    May 7, 2020

(30) Foreign Application Priority Data

Mar. 13, 2017 (JP) .............................. JP2017-047428
May 16, 2017 (JP) .............................. JP2017-097209
Nov. 8, 2017 (JP) .............................. JP2017-215697

(51) Int. Cl.
*C12Q 1/6848* (2018.01)
*C12N 15/10* (2006.01)
*C08B 37/16* (2006.01)
*C12P 19/34* (2006.01)
*C07J 41/00* (2006.01)
*C08B 30/18* (2006.01)

(52) U.S. Cl.
CPC ........ *C12Q 1/6848* (2013.01); *C07J 41/0027* (2013.01); *C08B 30/18* (2013.01); *C08B 37/0012* (2013.01); *C12N 15/1003* (2013.01); *C12P 19/34* (2013.01)

(58) Field of Classification Search
None
See application file for complete search history.

(56) References Cited

U.S. PATENT DOCUMENTS

| 5,705,345 | A  | 1/1998  | Lundin et al.   |
| 2010/0003531 | A1 | 1/2010  | Kikuchi et al.  |
| 2011/0256592 | A1 | 10/2011 | Beckers et al.  |
| 2013/0066062 | A1 | 3/2013  | Sano et al.     |
| 2014/0322761 | A1 | 10/2014 | Nakamura et al. |

FOREIGN PATENT DOCUMENTS

| JP | 2006-61041   | 3/2006  |
| JP | 2012-511317  | 5/2012  |
| JP | 2013-42750   | 3/2013  |
| JP | 2014-198029  | 10/2014 |
| JP | 2017-195871  | 11/2017 |
| WO | 2007/94506   | 8/2007  |
| WO | 2012/108471  | 8/2012  |

OTHER PUBLICATIONS

Holm et al., "Characterization of the complexation of tauro- and glyco-conjugated bile salts with c-cyclodextrin and 2-hydroxypropyl-c-cyclodextrin using affinity capillary electrophoresis" J Incl Phenom Macrocycl Chem vol. 61 pp. 161-169 DOI 10.1007/s10847-008-9409-5 (Year: 2008).*
Holm et al., "Complexation of tauro- and glyco-conjugated bile salts with three neutral beta-CDs studied by ACE" Electrophoresis vol. 28 pp. 3745-3752 DOI 10.1002/elps.200700311 (Year: 2007).*

* cited by examiner

*Primary Examiner* — Eric Olson
(74) *Attorney, Agent, or Firm* — Greenblum & Bernstein, P.L.C.

(57) ABSTRACT

The present invention addresses the problem of providing a reagent for extracting/amplifying a nucleic acid of a nucleic acid extraction target, the reagent being characterized in that a nucleic acid is conveniently extracted quickly and efficiently from the nucleic acid extraction target and inhibition of a nucleic acid amplification reaction is minimized, and the problem of providing a method for extracting or amplifying a nucleic acid using said reagent. The problems are solved by using a kit for extracting and amplifying a nucleic acid of a nucleic acid extraction target from a sample containing the nucleic acid extraction target, the kit including (i) a nucleic acid extraction reagent containing at least a surfactant having a steroid skeleton, (ii) γ-cyclodextrin having a C1-4 hydroxyalkyl group, and (iii) a nucleic acid amplification reagent.

14 Claims, No Drawings
Specification includes a Sequence Listing.

REAGENT FOR EXTRACTING AND AMPLIFYING NUCLEIC ACID

SEQUENCE LISTING

The instant application contains a Sequence Listing which has been filed electronically in ASCII format and is hereby incorporated by reference in its entirety. Said ASCII copy, created on Oct. 29, 2019, is named P58566_SL.txt and is 11,451 bytes in size.

FIELD

The present invention relates to a reagent for conveniently, rapidly and highly efficiently extracting and amplifying a nucleic acid, and a method for extracting and amplifying a nucleic acid using the reagent.

BACKGROUND

In the field of clinical examination on infectious disease, it is important to conveniently and rapidly detect pathogens with high sensitivity, and rapid test kits are widely available. A detection method using nucleic acid amplification techniques is known as a method for detecting pathogens with high sensitivity. When pathogens are detected with such a detection method using nucleic acid amplification techniques, nucleic acid extraction from a sample containing pathogens is generally performed in advance. A method known to be employed in such a case involves extracting nucleic acids from a pathogen using a surfactant, neutralizing the inhibitory effect of the surfactant on nucleic acid amplification reaction with the use of cyclodextrin, and subjecting the nucleic acids to a step of amplifying the nucleic acids.

In PTL 1, α, β, γ-cyclodextrin derivatives prepared through modification with functional groups are listed as components of a reagent for nucleic acid amplification reaction, and C1-4 hydroxyalkyl group or the like is illustrated as a functional group. PTL 1 further describes that PCR is performed under the coexistence of 2-hydroxypropyl-β-cyclodextrin added herein and a surfactant such as deoxycholic acid Na, and then the resistance of DNA polymerase against inhibitory effect is improved by the addition of cyclodextrin. However, PTL 1 does not describe specifically, γ-cyclodextrin having a C1-4 hydroxyalkyl group as cyclodextrin.

CITATION LIST

Patent Literature

[PTL 1] Japanese Unexamined Patent Publication (Kokai) No. 2014-198029

SUMMARY

Technical Problem

An object of the present invention is to provide a reagent for extracting and amplifying a nucleic acid, whereby a nucleic acid is extracted from a nucleic acid extraction target such as a microorganism conveniently, rapidly and highly efficiently, and the inhibition of the nucleic acid amplification reaction is minimized.

Solution to Problem

As a result of intensive studies to achieve the above object, the present inventors have completed the present invention. Specifically, the present invention encompasses the following embodiments.

<1> A kit for extracting and amplifying a nucleic acid of a nucleic acid extraction target from a sample containing the nucleic acid extraction target, including the following (i), (ii) and (iii), wherein the nucleic acid extraction target is selected from microorganisms, animal cells, plant cells and, extracellular vesicles:
 (i) a nucleic acid extraction reagent, containing at least a surfactant with a steroid skeleton;
 (ii) γ-cyclodextrin having a C1-4 hydroxyalkyl group; and
 (iii) a nucleic acid amplification reagent.

<2> The kit according to <1>, wherein the γ-cyclodextrin having a C1-4 hydroxyalkyl group is 2-hydroxypropyl-γ-cyclodextrin.

<3> The kit according to <1> or <2>, wherein the γ-cyclodextrin having a C1-4 hydroxyalkyl group is contained in the nucleic acid amplification reagent.

<4> The kit according to any one of <1> to <3>, wherein the concentration of the γ-cyclodextrin having a C1-4 hydroxyalkyl group is 4 or more times the concentration of the surfactant with a steroid skeleton.

<5> The kit according to any one of <1> to <4>, wherein the nucleic acid extraction target is a microorganism.

<6> A method for extracting and amplifying a nucleic acid of a nucleic acid extraction target from a sample containing the nucleic acid extraction target, including the following steps (i), (ii) and (iii), wherein the nucleic acid extraction target is selected from microorganisms, animal cells, plant cells, and extracellular vesicles:
 (i) a nucleic acid extraction step, which involves contacting a sample containing a nucleic acid extraction target with a nucleic acid extraction reagent containing at least a surfactant with a steroid skeleton, thereby obtaining a nucleic acid extract;
 (ii) a step of contacting the nucleic acid extract obtained in (i) with γ-cyclodextrin having a C1-4 hydroxyalkyl group; and
 (iii) a nucleic acid amplification step, which involves contacting the solution obtained in (ii) with a nucleic acid amplification reagent.

<7> A method for extracting and amplifying a nucleic acid of a nucleic acid extraction target from a sample containing the nucleic acid extraction target, including the following steps (i) and (ii), wherein the nucleic acid extraction target is selected from microorganisms, animal cells, plant cells, and extracellular vesicles:
 (i) a nucleic acid extraction step, which involves contacting a sample containing the nucleic acid extraction target with a nucleic acid extraction reagent containing at least a surfactant with a steroid skeleton, thereby obtaining a nucleic acid extract; and
 (ii) a nucleic acid amplification step, which involves contacting the nucleic acid extract obtained in (i) with a nucleic acid amplification reagent containing γ-cyclodextrin having a C1-4 hydroxyalkyl group.

<8> The method according to <6> or <7>, wherein the nucleic acid extraction target is a microorganism.

The present invention will be described more specifically as follows.

In the present invention, the term "surfactant with a steroid skeleton" refers to a compound having a cyclopentanoperhydrophenanthrene structure and the effect of surface activity. An example of a naturally existing surfactant with a steroid skeleton is bile acid. Bile acid is a steroid derivative having a cholanic acid skeleton, and often binds to glycine or taurine, so as to form conjugated bile acid. Examples of naturally existing bile acid and bile acid derivatives can include cholic acid, chenodeoxycholic acid, deoxycholic acid, lithocholic acid, tauroursodeoxycholic acid, taurocholic acid, glycocholic acid and salts thereof. Examples of such salts can include, but are not particularly limited to sodium salts. Further, examples of a surfactant in the present invention may include, not only naturally existing steroid derivatives and bile acid derivatives, but also artificially synthesized surfactants having steroid skeletons or cholanic acid skeleton. Particularly suitable examples of a surfactant in the present invention include cholic acid, taurocholic acid, glycocholic acid, tauroursodeoxycholic acid and salts thereof, and more preferably cholic acid and a salt thereof, and particularly sodium cholate. Note that the concentration of the surfactant with a steroid skeleton is not particularly limited. When a nucleic acid is extracted from a nucleic acid extraction target such as a microorganism, the concentration is preferably 0.4 (w/w) % or more, more preferably 1.0 (w/w) % or more, and further preferably 1.5 (w/w) % or more. The upper limit thereof is not particularly limited, and the concentration is preferably 10.0 (w/w) % or less, more preferably 5.0 (w/w) % or less, and further preferably 3.0 (w/w) % or less.

Examples of the nucleic acid extraction target of the present invention include microorganisms, animal cells, plant cells, and, and extracellular vesicles, but are not limited to organisms and broadly include those enclosing nucleic acids in membranes. Particularly preferable examples thereof include those extracted using a surfactant with a steroid skeleton. Further, upon extraction, extraction may be accelerated using a cell wall lytic enzyme, protease, a phospholipid-degrading enzyme, or the like. Furthermore, extraction is also preferably accelerated by the physical action by the use of zirconia powder, heating, pH changes, osmotic pressure, or the like.

Here, a nucleic acid may be DNA or RNA. Examples of the membrane include, in addition to capsids and cell walls, envelopes, and lipid bilayer membranes such as cell membranes. Further, examples of microorganisms include viruses, *Mycoplasma*, bacteria, and fungi. Examples of extraction targets include preferably viruses and *Mycoplasma*. A virus has a structure such that a protein shell referred to as capsid encloses the nucleic acid. Because of the structure, extraction of the nucleic acid has been difficult with the use of a conventional extraction method. Through application of the extraction method of the present invention, nucleic acids can be extracted conveniently and rapidly. The type of a virus to be extracted is not limited. Examples of a preferable extraction target virus include viruses having envelopes and viruses having single-stranded RNA. The term "viruses having envelopes" refers to viruses, wherein viral capsids are covered by envelopes mainly composed of lipids, and examples thereof include herpes simplex virus, influenza virus, RS virus, and AIDS virus (HIV). The term "viruses having single-stranded RNA" refers to viruses belonging to, on the basis of the Baltimore classification, Group 4 (single-stranded RNA+ strand), Group 5 (single-stranded RNA– strand), or Group 6 (single-stranded RNA reverse transcription). Examples thereof include Coronavirus, RS virus, human metapneumovirus, influenza virus, and AIDS virus (HIV). Viruses having single-stranded RNA are preferred in that these viruses are appropriate for nucleic acid amplification techniques such as TRC method using RNA as a starting material. Of these examples, influenza virus is particularly preferable as an extraction target virus for the extraction reagent of the present invention.

The term "*Mycoplasma*" in the present invention refers to those belonging to the genus *Mycoplasma* and examples thereof can include *Mycoplasma hyorhinis, Mycoplasma pneumoniae, Acheloplasma laidlawii, Mycoplasma fermentans, Mycoplasma orale, Spiroplasma citri, Mycoplasma synoviae, Mycoplasma gallisepticum*, and *Mycoplasma arginine*.

The term "*Mycoplasma* nucleic acid" in the present invention refers to a nucleic acid of *Mycoplasma*, and examples thereof can include genome, plasmids, mRNA, and rRNA. Because of the number of copies per cell and sequence specificity, rRNA is particularly preferable and 23S rRNA is most preferable.

Examples of the sample containing a nucleic acid extraction target in the present invention include a solution prepared by simply dissolving a nucleic acid extraction target in water, physiological saline or a buffer solution, a biological sample itself containing a nucleic acid extraction target, and filter paper, swab or the like containing the biological sample. Examples of the biological sample include blood, feces, urine, sputum, lymph, plasma, ejaculates, lung aspirates, cerebrospinal fluids, pharyngeal swabs, nasopharyngeal swabs, mouth rinses, saliva, and lacrimal fluids.

The nucleic acid extraction reagent of the present invention may further contain various components in addition to a surfactant with a steroid skeleton. The reagent containing components required for nucleic acid amplification reaction to be performed later, for example, an enzyme, a salt such as a magnesium salt and a potassium salt, a saccharide such as trehalose, sugar alcohol such as glycerol, nucleic acid components, and an organic solvent is preferable in that the operation from the nucleic acid extraction step to the nucleic acid amplification step can be simplified. Of these, an organic solvent is particularly preferable in that it has an effect of accelerating the nucleic acid extraction. An example of an organic solvent to be further contained in the extraction reagent of the present invention is dimethyl sulfoxide (DMSO). Further, in addition to a surfactant with a steroid skeleton, one or more types of surfactant or protein denaturant can also be added to such an extent that nucleic acid amplification reaction is not disturbed. Examples of a surfactant to be added include anionic surfactants such as SDS, amphoteric surfactants such as CHAPS (3-[(3-Cholamidopropyl)dimethylammonio]propanesulfonate), and nonionic surfactants such as SPAN™ 20 (Sigma Aldrich), MEGA-8 (Sigma Aldrich), polyoxyethylene sorbitan fatty acid ester (TWEEN™ 20 (Sigma Aldrich), TWEEN™ 40 (Sigma Aldrich), TWEEN™ 60 (Sigma Aldrich), and TWEEN™ 80 (Sigma Aldrich) etc.). Of these, a nonionic surfactant is preferable in that it has an effect of accelerating nucleic acid extraction and a reduced effect on nucleic acid amplification reaction. Examples of a surfactant to be added can include TWEEN™ 20 (Sigma Aldrich) which is a polyoxyethylene sorbitan fatty acid ester surfactant.

In order to extract a nucleic acid of a nucleic acid extraction target from a sample containing the nucleic acid extraction target using the nucleic acid extraction reagent of the present invention, the nucleic acid extraction reagent of the present invention may be simply contacted with a sample containing the nucleic acid extraction target. The duration of contact may be adequately determined in view of the properties of a sample containing a nucleic acid extraction target, the concentration of a nucleic acid extraction target in a sample, components contained in the nucleic acid extraction reagent, and the like. In many cases, the nucleic acid of a nucleic acid extraction target can be sufficiently extracted within 4 minutes after contact, and can also be subjected to a downstream step immediately after the contact, such as a step for contact with a cyclodextrin derivative.

In the method for extracting and amplifying a nucleic acid of the present invention, a nucleic acid extract of a nucleic acid extraction target can be obtained using a sample containing the nucleic acid extraction target and a nucleic acid extraction reagent. Subsequently, the nucleic acid extract is contacted with γ-cyclodextrin having a C1-4 hydroxyalkyl group, a surfactant with a steroid skeleton in the nucleic acid extract is enclosed in γ-cyclodextrin having a C1-4 hydroxyalkyl group, and thus the inhibitory effect on nucleic acid amplification reaction is alleviated. Therefore, according to the method for extracting and amplifying a nucleic acid of the present invention, a nucleic acid extract obtained in the step of extracting a nucleic acid can be conveniently subjected to an amplification step.

Examples of γ-cyclodextrin having a C1-4 hydroxyalkyl group include, but are not particularly limited to, γ-cyclodextrin having a
1-hydroxymethyl group
1-hydroxyethyl group
2-hydroxyethyl group
1-hydroxypropyl group
2-hydroxypropyl group
3-hydroxypropyl group
2-hydroxy-1-methyl-ethyl group
1-hydroxybutyl group
2-hydroxybutyl group
3-hydroxybutyl group
4-hydroxybutyl group
1-hydroxy-2-methyl-propyl group
2-hydroxy-1-methyl-propyl group
3-hydroxy-1-methyl-propyl group
1-hydroxy-2-methyl-ethyl group
2-hydroxy-1,2-dimethyl-ethyl group
1,2-dihydroxy-ethyl group
1,2-dihydroxy-propyl group
2,3-dihydroxy-propyl group
1,2-dihydroxy-butyl group
2,3-dihydroxy-butyl group
3,4-dihydroxy-butyl group
1,2,3-trihydroxy-butyl group
2,3-dihydroxy-1-methyl-propyl group, or the like.
Of these examples, a 1-hydroxypropyl group, a 2-hydroxypropyl group, and a 3-hydroxypropyl group are preferable, and particularly 2-hydroxypropyl-γ-cyclodextrin is preferable.

Further, γ-cyclodextrin having a C1-4 hydroxyalkyl group may be in any form of solution, solid, and the like. Furthermore, upon contact of the nucleic acid extract of the present invention with γ-cyclodextrin having a C1-4 hydroxyalkyl group, the extract may be contacted simultaneously with other various components.

After contact of a reagent for extracting microbial nucleic acid with a sample containing a nucleic acid extraction target, the γ-cyclodextrin having C1-4 hydroxyalkyl group is contacted with the thus obtained nucleic acid extract. This may be achieved before contact with or simultaneously with the contact with a nucleic acid amplification reagent, and the way of contact can be adequately selected within the above range depending on required extraction efficiency. A particularly suitable example of an embodiment of the present invention can be a method that involves contacting the γ-cyclodextrin having C1-4 hydroxyalkyl group with a nucleic acid extract, simultaneously with the contact with a nucleic acid amplification reagent. Furthermore, simultaneous addition of the γ-cyclodextrin having a C1-4 hydroxyalkyl group and a nucleic acid amplification reagent is further preferable in view of more convenient operation, and thus a nucleic acid amplification reagent containing the γ-cyclodextrin having a C1-4 hydroxyalkyl group can also be used herein.

Note that the nucleic acid amplification reagent contains components required for nucleic acid amplification reaction, and can contain, for example, an enzyme, salts such as a magnesium salt and a potassium salt, saccharides such as trehalose, sugar alcohols such as glycerol, nucleic acid components, organic solvents, nucleic acids such as primers and probes, and components of a buffer solution. An example of a suitable embodiment of the present invention is a reagent with which nucleic acid amplification reaction is performed when a nucleic acid of a nucleic acid extraction target is extracted using a nucleic acid extraction reagent containing a surfactant with a steroid skeleton, and then the thus obtained nucleic acid extract is added to a nucleic acid amplification reagent containing the γ-cyclodextrin having a C1-4 hydroxyalkyl group. In addition, the concentration of the γ-cyclodextrin having a C1-4 hydroxyalkyl group is not particularly limited, and is preferably 4 or more times and more preferably 5 or more times the concentration of a surfactant with a steroid skeleton. The upper limit thereof is not particularly limited, and is preferably 13 or less times, and further preferably 8 or less times the concentration of a surfactant with a steroid skeleton.

A nucleic acid amplification technique in the present invention may be any nucleic acid amplification technique (for example, PCR method, TMA method, TRC method, and NASBA method). A method that involves performing nucleic acid amplification isothermally is preferable since it does not require a relatively complicated apparatus for increasing and decreasing the temperature. An example of such a nucleic acid amplification technique is a method for amplifying a target nucleic acid using a first primer having a sequence homologous to a portion of a nucleic acid of the nucleic acid extraction target, a second primer having a sequence complementary to a portion of a nucleic acid of the nucleic acid extraction target, an enzyme having RNA-dependent DNA polymerase activity, an enzyme having DNA-dependent DNA polymerase activity, an enzyme having ribonuclease H (RNase H) activity, and an enzyme having RNA polymerase activity, wherein a promoter sequence corresponding to the enzyme having RNA polymerase activity is added to the 5' end side of the first primer or the second primer (for example, TMA method, TRC method, or NASBA method). This is a method for amplifying a nucleic acid using single-stranded RNA as a target. Double-stranded DNA or the like can also be amplified using the method disclosed in Japanese Unexamined Patent Publication (Kokai) No. 2015-11636, for example.

The nucleic acid amplification reagent in the present invention may be in a dry state. The nucleic acid amplification reagent contains an enzyme, and thus drying the reagent can extend the storage period longer than that of the reagent in a liquid state, and can realize a proper storage temperature closer to room temperature. Drying the reagent has an advantage such that it can be easily treated upon transport or use.

A method for making the reagent in a dry state may be any method as long as enzymatic activity is not lost, and examples thereof can include a freeze-drying method and a method for evaporation to dryness.

Advantageous Effects of Invention

According to the present invention, contact of γ-cyclodextrin having a C1-4 hydroxyalkyl group with a surfactant can reduce the inhibitory effect of the surfactant on enzymatic reaction with significantly high efficiency, compared with a case of contact with another cyclodextrin derivative. Therefore, according to the method for extracting and amplifying a nucleic acid of the present invention, a nucleic acid extract obtained in the step of extracting a nucleic acid can be conveniently subjected to an amplification step.

EXAMPLES

The present invention will be described in greater detail as follows with reference to examples and referential examples of the use of influenza virus or *Mycoplasma pneumoniae* as nucleic acid extraction targets, but the present invention is not limited by these examples.

Example 1 Preparation of Standard RNA

Primers, influenza virus RNA (hereinafter, denoted as "standard RNA") and intercalating fluorescent dye standard nucleic acid probes used in the following examples were prepared by the methods described in Japanese Unexamined Patent Publication (Kokai) No. 2016-131498.

Example 2 Inclusion Effect of Cyclodextrin Derivative

The inclusion effects of cyclodextrin derivatives on a surfactant were examined by the following method.
(1) Type A (subtype H1N1) influenza virus standard RNA prepared in Example 1 was diluted with water for injection so that the concentration was $10^3$ copies/2.5 μL, and then the resultant was used as an RNA sample.
(2) The RNA sample (2.5 μL) prepared in (1) was added to 12.5 μL of a surfactant-containing solution (hereinafter, denoted as "viral extract") composed of the following composition and preheated at 46° C. The solution was agitated and maintained at 46° C. for 4 minutes, thereby preparing 15 μL of viral RNA extract.
Composition of a viral extract: The concentration thereof was the final concentration after addition of a virus sample (in 15 μL).

44.4 mM magnesium chloride
110 mM potassium chloride
2.4% glycerol
22.0% DMSO
0.1% (v/v) Tween20
1.5% (w/w) sodium cholate.

(3) A cyclodextrin derivative-containing reaction solution (15 μL) composed of the following composition was dispensed to 0.5-mL PCR tubes (Individual Dome Cap PCR Tube, SSI and then maintained at 46° C. for 4 minutes. Immediately after 4 minutes of maintaining the temperature at 46° C., 15 μL of the viral RNA extract obtained in (2) was added. In addition, as first primers and second primers, oligonucleotides having sequences and concentrations listed in Table 1 were used in combination. Further, to each first primer, T7 promoter sequence (SEQ ID NO: 3) was added to the 5' end side of the nucleotide sequence described in each SEQ ID NO listed in Table 1.

TABLE 1

| | SEQ ID NO: | Concentration | Remarks |
|---|---|---|---|
| First primer | 1 | 0.4 μM | Nucleotide 616 to nucleotide 635 of the nucleotide sequence under GenBank No. FJ969536 (for type A (subtype H1N1)) |
| | 4 | 0.2 μM | Nucleotide 662 to nucleotide 681 of the nucleotide sequence under GenBank No. KJ741989 (for type A (subtype H3N2)) |
| | 6 | 0.6 μM | Nucleotide 432 to nucleotide 452 of the nucleotide sequence under GenBank No. CY115184 (for type B) |
| Second primer | 2 | 0.4 μM | Complementary strand of nucleotide 717 to nucleotide 743 of the nucleotide sequence under GenBank No. FJ969536 (for type A (subtype H1N1)) |
| | 5 | 0.2 μM | Complementary strand of nucleotide 762 to nucleotide 788 of the nucleotide sequence under GenBank No. KJ741989 (for type A (subtype H3N2)) |
| | 7 | 0.6 μM | Complementary strand of nucleotide 543 to nucleotide 565 of the nucleotide sequence under GenBank No. CY115184 (for type B) |

Composition of reaction solution: The concentration was the final concentration after addition of viral RNA extract (in 30 μL).

60 mM Tris-HCl (pH 8.6)
0.25 mM each: dATP, dCTP, dGTP and dTTP
2.7 mM each: ATP, CTP, UTP and GTP
3.06 mM ITP
70 mM trehalose
9.1 U AMV reverse transcriptase
142 U T7 RNA polymerase
20 nM each INAF probe (prepared in Example 1)

First primer (for type A (subtype H1N1)) with the concentration described in Table 1
Second primer (for type A (subtype H1N1)) with the concentration described in Table 1
Cyclodextrin derivatives with concentrations each described in Table 2 to Table 11
(4) Subsequently, with the use of a spectrophotofluorometer (TRC RAPID-160™, TOSOH CORPORATION) having a temperature-controlling function and being capable of directly measuring PCR tubes, the fluorescence intensity (excitation wavelength: 470 nm, and fluorescent wavelength: 520 nm) of the reaction solution was measured over time for 30 minutes simultaneously with reaction at 46° C. A case where the fluorescence intensity ratio (the value obtained by dividing the value of the fluorescence intensity at a predetermined time by the value of the fluorescence intensity of the background) of the reaction solution was higher than 1.2 was determined positive. The time upon mixing with the reagent was designated as 0 minutes, and the time required to obtain a positive determination was designated as the detection time.
The results are depicted in Table 2 to Table 11.

TABLE 2

| Cyclodextrin derivative | Final concentration (in 30 μL) | Detection time (mm) |
|---|---|---|
| 2-hydroxypropyl-γ-cyclodextrin | 2 | N.D. |
| | 4 | N.D. |
| | 6 | N.D. |

TABLE 2-continued

| Cyclodextrin derivative | Final concentration (in 30 μL) | Detection time (min) |
|---|---|---|
|  | 6.8 | 4.50 |
|  | 8 | 3.56 |
| γ-cyclodextrin | 6.8 | 4.13 |
| No addition | 0 | N.D. |

TABLE 3

| Cyclodextrin derivative | Final concentration (in 30 μL) | Detection time (min) |
|---|---|---|
| 2-hydroxypropyl-γ-cyclodextrin | 8 | 4.21 |
|  | 10 | 3.67 |
|  | 12 | 3.70 |
|  | 14 | 4.09 |
| γ-cyclodextrin | 6.8 | 5.67 |
| No addition | 0 | N.D. |

TABLE 4

| Cyclodextrin derivative | Final concentration (in 30 μL) | Detection time (min) |
|---|---|---|
| 2-hydroxyethyl-β-cyclodextrin | 2 | N.D. |
|  | 4 | N.D. |
|  | 6 | N.D. |
|  | 8 | N.D. |
|  | 10 | N.D. |
|  | 12 | 8.96 |
|  | 14 | 5.08 |
|  | 16 | 5.38 |
| γ-cyclodextrin | 6.8 | 5.00 |
| No addition | 0 | N.D. |

TABLE 5

| Cyclodextrin derivative | Final concentration (in 30 μL) | Detection time (min) |
|---|---|---|
| 2-hydroxypropyl-β-cyclodextrin | 2 | N.D. |
|  | 4 | N.D. |
|  | 6 | N.D. |
|  | 8 | N.D. |
|  | 10 | 11.10 |
|  | 12 | 7.48 |
|  | 14 | 6.02 |
|  | 16 | 6.39 |
| γ-cyclodextrin | 6.8 | 5.00 |
| No addition | 0 | N.D. |

TABLE 6

| Cyclodextrin derivative | Final concentration (in 30 μL) | Detection time (min) |
|---|---|---|
| Methyl-β-cyclodextrin | 2 | N.D. |
|  | 4 | N.D. |
|  | 6 | N.D. |
|  | 8 | N.D. |
|  | 10 | N.D. |
|  | 12 | N.D. |
|  | 14 | N.D. |
|  | 16 | N.D. |
| γ-cyclodextrin | 6.8 | 5.02 |
| No addition | 0 | N.D. |

TABLE 7

| Cyclodextrin derivative | Final concentration (in 30 μL) | Detection time (min) |
|---|---|---|
| 2-hydroxypropyl-α-cyclodextrin | 2 | N.D. |
|  | 4 | N.D. |
|  | 6 | N.D. |
|  | 8 | N.D. |
|  | 10 | N.D. |
|  | 12 | N.D. |
|  | 14 | N.D. |
|  | 16 | N.D. |
| γ-cyclodextrin | 6.8 | 5.29 |
| No addition | 0 | N.D. |

TABLE 8

| Cyclodextrin derivative | Final concentration (in 30 μL) | Detection time (min) |
|---|---|---|
| Monoacetyl-β-cyclodextrin | 2 | N.D. |
|  | 4 | N.D. |
|  | 6 | N.D. |
|  | 8 | N.D. |
|  | 10 | N.D. |
|  | 12 | N.D. |
|  | 14 | N.D. |
|  | 16 | N.D. |
| γ-cyclodextrin | 6.8 | 5.80 |
| No addition | 0 | N.D. |

TABLE 9

| Cyclodextrin derivative | Final concentration (in 30 μL) | Detection time (min) |
|---|---|---|
| 3A-amino-3A-deoxy-(2AS,3AS)-γ-cyclodextrin | 2 | N.D. |
|  | 4 | N.D. |
|  | 6 | N.D. |
|  | 8 | N.D. |
|  | 10 | N.D. |
|  | 12 | N.D. |
|  | 14 | N.D. |
|  | 16 | N.D. |
| γ-cyclodextrin | 6.8 | 5.93 |
| No addition | 0 | N.D. |

TABLE 10

| Cyclodextrin derivative | Final concentration (in 30 μL) | Detection time (min) |
|---|---|---|
| Mono-2-O-(p-toluenesulfonyl)-γ-cyclodextrin | 2 | N.D. |
|  | 4 | N.D. |
|  | 6 | N.D. |
|  | 8 | N.D. |
|  | 10 | N.D. |
|  | 12 | N.D. |
|  | 14 | N.D. |
|  | 16 | N.D. |
| γ-cyclodextrin | 6.8 | 5.28 |
| No addition | 0 | N.D. |

TABLE 11

| Cyclodextrin derivative | Final concentration (in 30 μL) | Detection time (min) |
|---|---|---|
| γ-cyclodextrin phosphate | 2 | N.D. |
|  | 4 | N.D. |

TABLE 11-continued

| Cyclodextrin derivative | Final concentration (in 30 μL) | Detection time (min) |
|---|---|---|
|  | 6 | N.D. |
|  | 8 | N.D. |
|  | 10 | N.D. |
|  | 12 | N.D. |
|  | 14 | N.D. |
|  | 16 | N.D. |
| γ-cyclodextrin | 6.8 | 5.14 |
| No addition | 0 | N.D. |

2-hydroxypropyl-γ-cyclodextrins of Table 2 and Table 3 were confirmed to exhibit the inclusion effect at 6.8% (w/w) or more, to exhibit the shortest time required for a positive determination at 10% (w/w), suggesting the high effect at 10% (w/w), and to exhibit the effect at 8% (w/w) higher than that of 6.8% (w/w) γ-cyclodextrin.

2-hydroxyethyl-β-cyclodextrin of Table 4 was confirmed to exhibit the inclusion effect at 12% (w/w) or more, and to exhibit the shortest time required for a positive determination at 14% (w/w), suggesting the high effect at 14% (w/w), but to never exhibit the time required for a positive determination shorter than that of 6.8% (w/w) γ-cyclodextrin.

2-hydroxypropyl-β-cyclodextrin of Table 5 was confirmed to exhibit the inclusion effect at 10% (w/w) or more, and to exhibit the shortest time required for a positive determination at 14% (w/w), suggesting the high effect at 14% (w/w), but to never exhibit the time required for a positive determination shorter than that of 6.8% (w/w) γ-cyclodextrin.

Methyl-β-cyclodextrin of Table 6, 2-hydroxypropyl-α-cyclodextrin of Table 7, monoacetyl-β-cyclodextrin of Table 8, 3A-amino-3A-deoxy-(2AS, 3AS)-γ-cyclodextrin of Table 9, mono-2-O-(p-toluenesulfonyl)-γ-cyclodextrin of Table 10, and γ-cyclodextrin phosphate of Table 11 were confirmed to exhibit no inclusion effect at any concentration described in each Table.

Example 3 Method for Preparing Amplification Reagent Evaporated to Dryness

A 2-hydroxypropyl-γ-cyclodextrin-containing reagent solution (18.5 μL) composed of the following composition was dispensed to 0.5-mL PCR tubes (Individual Dome Cap PCR Tube, SSI), and then evaporated to dryness in VIRTIS ADVANTAGE PLUS™ at 25° C. and 100 torr for 16 hours, and then at 50° C. for 1.5 hours until the temperature within the freeze dryer was stable at 25° C. In addition, as first primers and second primers, oligonucleotides having sequences and concentrations listed in Table 1 were used in combination as appropriate. Specifically, in preparation of a reagent for detection of type A (subtype H1N1), a primer including the nucleotide sequence of SEQ ID NO: 1 and a primer including the nucleotide sequence of SEQ ID NO: 2 were used in combination. In preparation of a reagent for detection of type A (subtype H3N2), a primer including the nucleotide sequence of SEQ ID NO: 4 and a primer including the nucleotide sequence of SEQ ID NO: 5 were used in combination. In preparation of a reagent for detection of type B, a primer including the nucleotide sequence of SEQ ID NO: 6 and a primer including the nucleotide sequence of SEQ ID NO: 7 were used in combination. Further, to each first primer, T7 promoter sequence (SEQ ID NO: 3) was added to the 5' end side of the nucleotide sequence described in each SEQ ID NO listed in Table 1. Amplification reagents after drying were sealed and then stored with a drying agent at 4° C.

Composition of reagent solution: The concentration was the final concentration of TRC reaction (in 30 μL).

6 mM Tris-HCl (pH 8.65)
0.25 mM each: dATP, dCTP, dGTP and dTTP
2.7 mM each: ATP, CTP, UTP and GTP
3.06 mM ITP
198.9 mM trehalose
9.1 U AMV reverse transcriptase
142 U T7 RNA polymerase
20 nM each INAF probe (prepared in Example 1)

First primer with the concentration described in Table 1
Second primer with the concentration described in Table 1
2-hydroxypropyl-γ-cyclodextrin at each concentration of 5.2% (w/w), 6.7% (w/w), 8.2% (w/w), 9.7% (w/w), 11.2% (w/w), and 12.7% (w/w).

Example 4 Evaluation of Amplification Reagent Evaporated to Dryness

A cyclodextrin derivative-containing amplification reagent evaporated to dryness in the present invention was evaluated by the following method.

(1) Type A (subtype H1N1) influenza virus standard RNA prepared in Example 1 was diluted with water for injection, so that the concentration was $10^3$ copies/2.5 μL, and then the resultant was used as an RNA sample.

(2) The RNA sample (2.5 μL) prepared in (1) was added to 27.5 μL of a viral extract composed of the following composition. The solution was agitated and maintained at 46° C. for 4 minutes.

Composition of a viral extract (liquid): The concentration was the final concentration upon addition of 2.5 μL of RNA sample (in 30 μL).

22.2 mM magnesium chloride
55.0 mM potassium chloride
1.2% glycerol
11.0% DMSO
0.05% (v/v) Tween20
1.5% (w/w) sodium cholate
54 mM Tris-HCl (pH 8.65)
4 mM Tris (2-carboxyethyl)phosphine hydrochloride
3 mM KOH 4 mM Tris (2-carboxyethyl)phosphine hydrochloride
3 mM KOH (3) The viral extract (30 μL) of (2) was added to and mixed with the amplification reagent evaporated to dryness (for type A (subtype H1N1)), which had been prepared in Example 3.

(4) Measurement was performed in a manner similar to Example 2 (4). The results are depicted in Table 12.

TABLE 12

| 2-hydroxypropyl-γ-cyclodextrin concentration | Detection time (min) |
|---|---|
| 5.2% | 10.5 |
| 6.7% | 5.5 |
| 8.2% | 4.4 |
| 9.7% | 4.6 |

TABLE 12-continued

| 2-hydroxypropyl-γ-cyclodextrin concentration | Detection time (min) |
|---|---|
| 11.2% | 5.1 |
| 12.7% | 7.2 |

TRC reaction was confirmed for the amplification reagent evaporated to dryness containing 2-hydroxypropyl-γ-cyclodextrin at a concentration of at least 5.2%, and the reagent containing the same at 8.2% exhibited the shortest detection time.

Example 5 Detection Sensitivity of Amplification Reagent Evaporated to Dryness for Influenza Virus Various influenza viruses were detected by the following method using the reagent for extracting/amplifying a nucleic acid of the present invention.

(1) influenza viruses listed in Table 13 were diluted with water for injection at concentrations listed in Table 14, thereby preparing virus samples.

(2) Each virus sample (50 μL) prepared in (1) was added to 1000 μL of a viral extract composed of the following composition. The resultant was agitated and then maintained at 46° C. for 4 minutes.

Composition of a viral extract:

22.2 mM magnesium chloride
75.0 mM potassium chloride
1.2% glycerol
11.0% DMSO
0.05% (v/v) Tween20
1.5% (w/w) sodium cholate
54 mM Tris-HCl (pH 8.65)
4 mM Tris (2-carboxyethyl)phosphine hydrochloride
3 mM KOH (3) The viral extract (30 μL) of (2) was added to and mixed with each of 8.2% 2-hydroxypropyl-γ-cyclodextrin-containing reagents evaporated to dryness (the reagent for detection of type A (subtype H1N1), the reagent for detection of type A (subtype H3N2), and the reagent for detection of type B) prepared in Example 3.

(4) Measurement was performed in a manner similar to Example 2 (4). The results are depicted in Table 14.

TABLE 13

| Type | Strain |
|---|---|
| Type A (subtype H1N1) | A/California/07/2009 |
| Type A (subtype H3N2) | A/Texas/50/2012 |
| Type B | B/Massachusetts/2/2012 |

TABLE 14

| Detection target virus | Virus concentration [TCID$_{50}$/ml] | Detection time [min] |
|---|---|---|
| Type A Subtype H1N1 | $1.0 \times 10^0$ | 4.2 |
| | $1.0 \times 10^{-1}$ | 6.3 |
| Type A Subtype H3N2 | $1.0 \times 10^0$ | 3.3 |
| | $1.0 \times 10^{-1}$ | N.D. |
| Type B | $1.0 \times 10^1$ | 4.8 |
| | $1.0 \times 10^0$ | 6.7 |
| | $1.0 \times 10^{-1}$ | N.D. |

N.D.: not detected

As a result, it was demonstrated that various influenza viruses can be detected using the reagent for extracting/amplifying a nucleic acid of the present invention.

Example 6 Comparison of Performance Among Cyclodextrin Derivatives

Performance was compared among the cyclodextrin derivatives in the present invention by the following method.

(1) A 8.2% 2-hydroxypropyl-γ-cyclodextrin-containing reagent evaporated to dryness was prepared by the method described in Example 3. Further, a reagent evaporated to dryness containing 8.2% 2-hydroxypropyl-β-cyclodextrin instead of 2-hydroxypropyl-γ-cyclodextrin, and a reagent evaporated to dryness containing 8.2% 2-hydroxyethyl-β-cyclodextrin instead of 2-hydroxypropyl-γ-cyclodextrin were prepared respectively.

(2) H1N1 viral extract was prepared by the method described in (1) and (2) of Example 5.

(3) The above viral extract was added, 30 μL each, to and mixed with the 3 types of reagents evaporated to dryness of (1).

(4) Measurement was performed in a manner similar to Example 2 (4). The results are depicted in Table 15.

TABLE 15

| Reagent evaporated to dryness | H1N1 influenza virus concentration (TCID$_{50}$/mL) | | | |
|---|---|---|---|---|
| | 1000 | 100 | 10 | 1 |
| 2-hydroxypropyl-γ-cyclodextrin | — | 3.48 | 4.12 | 5.13 |
| 2-hydroxypropyl-β-cyclodextrin | 3.62 | 5.07 | 5.34 | 5.62 |
| 2-hydroxyethyl-β-cyclodextrin | — | N.D. | N.D. | N.D. |

Numerical value: TRC rise time
—: not performed
N.D.: not detected

As a result, 2-hydroxyethyl-β-cyclodextrin was not confirmed to exhibit any inclusion effect and detection could be not be performed. Detection was confirmed in the case of 2-hydroxypropyl-γ-cyclodextrin and 2-hydroxypropyl-β-cyclodextrin. Whereas the virus concentration, which could be detected within three-something minutes, was 1000 TCID$_{50}$/mL in the case of 2-hydroxypropyl-β-cyclodextrin, the same in the case of 2-hydroxypropyl-γ-cyclodextrin was 100 TCID$_{50}$/mL. Specifically, the virus concentration in the case of 2-hydroxypropyl-β-cyclodextrin was 10 times greater than the other.

Example 7 Preparation of Standard RNA

*Mycoplasma pneumoniae* standard samples to be used in examples below were prepared by the following method.

*Mycoplasma pneumoniae* Culture Solution

*Mycoplasma pneumoniae* was cultured according to the method described in "*Mycoplasma pneumoniae* detection manual" (National Institute of Infectious Diseases (NIID), September, 2011) using a modified Hayflick liquid medium supplemented with glucose. The culture solution was aseptically dispensed and then stored at −80° C. The CFU (colony forming unit)/mL of the thus prepared culture solution was calculated using a modified Hayflick agar medium supplemented with glucose.

Example 8 Preparation of Oligonucleotide Labeled with Intercalating Fluorescent Dye An oligonucleotide probe (hereinafter, described as "INAF probe") labeled with an intercalating fluorescent dye, as depicted in the following (A), was prepared based on the method disclosed in Japanese Unexamined Patent Publication (Kokai) No. 2000-316587.

(A) The probe was labeled with thiazole orange via a linker between the $4^{th}$ guanine and the $5^{th}$ cytosine from the 5' end of the oligonucleotide represented by the nucleotide sequence (nucleotide 2193 to nucleotide 2208 of the nucleotide sequence under GenBank No. NR_077056.1) described in SEQ ID NO: 8.

Example 9 Detection of *Mycoplasma Pneumoniae*

A combination of a first primer, a second primer and an INAF probe listed in Table 16 was used and evaluated by the following method. Note that the INAF probe described in Table 16 was a probe prepared in Example 8.

(1) Standard samples prepared in Example 7 were each diluted with physiological saline so that the concentrations were the final concentrations (CFU/test) listed in Table 17, and then used as detection samples.

(2) A reaction solution composed of the following composition was dispensed to tubes for evaporation to dryness and then evaporated to dryness.

Composition of amplification reagent: The concentration was the final concentration (in 30 μL) after addition of an RNA sample and an initiator solution.

60 mM Tris-HCl buffer solution (pH 8.35)
150 mM trehalose
0.48 mM each: dATP, dCTP, dGTP and dTTP
2.1 mM each: ATP, CTP, UTP and GTP
3.2 mM ITP
0.2 μM first primer (SEQ ID NO: 9)
0.2 μM second primer (SEQ ID NO: 10)
100 nM INAF probe (prepared in Example 2)
0.025 mg/mL bovine serum albumin
142 U T7 RNA polymerase
6.4 U AMV reverse transcriptase
8.2% (w/v) 2-hydroxypropyl-γ-cyclodextrin (3) Each detection sample (1 μL) prepared in (1) was added to 29 μL of *Mycoplasma* extract composed of the following composition, agitated, and then maintained at 46° C. for 1 minute.

Composition of *Mycoplasma* extract: The concentration was the final concentration (in 30 μL) when 1 μL of a detection sample was added.

21.0 mM magnesium chloride
50.0 mM potassium chloride
10.07% DMSO
0.05% (v/v) Tween20
1.5% (w/w) sodium cholate (4) Thirty (30) μL of the *Mycoplasma* extract of (3) was added to and mixed with the amplification reagent evaporated to dryness (for *Mycoplasma pneumoniae*) prepared in (2).

(5) Subsequently, with the use of a spectrophotometer having a temperature-controlling function and being capable of directly measuring the tubes for evaporation to dryness, the fluorescence intensity of the reaction solution was measured over time for 20 minutes simultaneously with reaction at 46° C.

The time upon completion of the addition of *Mycoplasma* extract and the agitation of the mixture was designated as 0 minutes. A case where the fluorescence intensity ratio (the value obtained by dividing the value of the fluorescence intensity at a predetermined time by the value of the fluorescence intensity of the background) of the reaction solution was higher than 1.2 was determined positive, and the time of this positive determination was designated as detection time. The results are depicted in Table 17. "N.D." in Table 17 means that the fluorescence intensity ratio at 20 minutes after the initiation of reaction was 1.5 or less (negative determination).

As a result, it was demonstrated that 23S rRNA of *Mycoplasma pneumoniae* can be rapidly detected with high sensitivity by the use of this method.

[Table 16]

TABLE 16

| | Sequence | Content |
|---|---|---|
| First primer | AATTCTAATACGACTCACTATA GGGAGACCCTTACACCATTACA CTCTAC | Primer for amplification of Mycoplasma nucleic acid, having T7 promoter sequence |
| Second primer | TTAATATTGATCAGGACATTAT CATGTAGA | Primer for amplification of Mycoplasma nucleic acid |
| INAF probe | TGTGCTGTTCTAATTG | Probe with fluorescent tag between the $4^{th}$ guanine and the $5^{th}$ cytosine from the 5' end |

TABLE 17

| Final concentration (CFU/test) | Detection time (min) | | | Average detection time (min) |
|---|---|---|---|---|
| 1000 | 5.29 | 5.39 | 5.17 | 5.28 |
| 100 | 6.79 | 5.95 | 6.13 | 6.29 |
| 10 | 7.96 | 8.11 | 7.98 | 8.02 |
| 1 | 12.87 | 8.92 | 10.31 | 10.7 |
| 0.1 | N.D. | N.D. | N.D. | N.D. |

Comparative Example 1 Examination of Cyclodextrin Derivatives in Detection of *Mycoplasma pneumoniae*

A combination of a first primer, a second primer and an INAF probe listed in Table 16 was used in a manner similar to Example 9 except for using cyclodextrin derivatives listed in Table 18 instead of 2-hydroxypropyl-γ-cyclodextrin, and then evaluation was performed by the following method. Note that the INAF probe described in Table 16 was the probe prepared in Example 8.

(1) Standard samples prepared in Example 7 were each diluted with physiological saline so that the concentrations were the final concentrations (CFU/test) listed in Table 17, and then used as detection samples.

(2) A reaction solution composed of the following composition was dispensed to tubes for evaporation to dryness and then evaporated to dryness.

Composition of amplification reagent: The concentration was the final concentration after addition of an RNA sample, an initiator solution (in 30 μL)

60 mM Tris-HCl buffer solution (pH 8.35)
150 mM trehalose
0.48 mM each: dATP, dCTP, dGTP and dTTP
2.1 mM each: ATP, CTP, UTP and GTP
3.2 mM ITP
0.2 μM first primer (SEQ ID NO: 9)
0.2 μM second primer (SEQ ID NO: 10)
100 nM INAF probe (prepared in Example 2)
0.025 mg/mL bovine serum albumin
142U T7 RNA polymerase
6.4 U AMV reverse transcriptase Cyclodextrin derivatives listed in Table 18

(3) One μL (1000 CFU/test) of the detection sample prepared in (1) was added to 29 μL of *Mycoplasma* extract composed of the following composition, agitated, and then maintained at 46° C. for 1 minute.

Composition of *Mycoplasma* extract: The concentration was the final concentration (in 30 μL) when 1 μL of a detection sample was added.

21.0 mM magnesium chloride
50.0 mM potassium chloride
10.07% DMSO
0.05% (v/v) Tween20
1.5% (w/w) sodium cholate (4) Thirty (30) μL of the *Mycoplasma* extract of (3) was added to and mixed with the amplification reagent evaporated to dryness (for *Mycoplasma pneumoniae*) prepared in (2).

(5) Subsequently, with the use of a spectrophotofluorometer having a temperature-controlling function and being capable of directly measuring the tubes for evaporation to dryness, the fluorescence intensity of the reaction solution was measured over time for 20 minutes simultaneously with reaction at 46° C.

The time upon completion of the addition of *Mycoplasma* extract and agitation was designated as 0 minutes. A case where the fluorescence intensity ratio (the value obtained by dividing the value of the fluorescence intensity at a predetermined time by the value of the fluorescence intensity of the background) of the reaction solution was higher than 1.2 was determined positive, and the time of this positive determination was designated as detection time. The results are depicted in Table 18, "N.D." in Table 18 means that the fluorescence intensity ratio at 20 minutes after the initiation of reaction was 1.5 or less (negative determination).

As a result, the use of derivatives other than γ-cyclodextrin resulted in negative determination and measurement could not be performed. The detection time in the case of γ-cyclodextrin was 8.89 minutes, revealing that the effect thereof was lower than that of 2-hydroxypropyl-γ-cyclodextrin.

TABLE 18

| Concentration (%(w/v)) | Cyclodextrin derivative name | Detection time (min) |
|---|---|---|
| 8.2 | 2-Hydroxypropyl-β-cyclodextrin | N.D. |
| 8.2 | Methyl-β-cyclodextrin | N.D. |
| 8.2 | Monoacetyl-β-cyclodextrin | N.D. |
| 8.2 | 2-Hydroxyethyl-β-cyclodextrin | N.D. |
| 8.2 | γ-cyclodextrin | 8.89 |
| 8.2 | 2-Hydroxypropal-α-cydodextrin | N.D. |
| 8.2 | 3A-Amino-3A-deoxy-(2AS,3As)-γ-cyclodextrin | N.D. |
| 8.2 | Mono-2-O-(p-toluenesulfonyl)-γ-cyclodextrin | N.D. |
| 8.2 | 2-Hydroxypropyl-α-cyclodextrin | N.D. |

Example 10 Real-Time PCR

Recovery from reaction inhibition by sodium cholate and that from reaction inhibition by 2-hydroxypropyl-γ-cyclodextrin in real-time PCR were evaluated by the following method.

(1) A reagent with the reaction composition described in Table 19 was prepared on a 96-well PCR plate (Applied biosystems) and then sealed with 8 cap strips (Applied biosystems).

(2) Next, with the use of Quant Studio 5 (Applied biosystems), after heating at 95° C. for 30 seconds, 40 cycles (95° C. for 10 seconds, 60° C. for 34 seconds) of amplification reaction was performed to calculate Ct value. The results are depicted in Table 20.

As a result, at least 0.5% sodium cholate contained completely inhibited real-time PCR. On the other hand, it was demonstrated that even in the case of adding 1.5% sodium cholate, addition of 8.2% 2-hydroxypropyl-γ-cyclodextrin alleviates the reaction inhibition and real-time PCR can be performed.

It was confirmed by the above results that nucleic acid amplification in the present invention is also applicable to real-time PCR.

TABLE 19

| Reagent | Amount of reagent used (μL) | Purchased from SEQ ID NO: |
|---|---|---|
| SYBR Premix Ex Taq II | 10 | Takara Bio Inc. |
| ROX Reference Dye II | 0.4 | Takara Bio Inc. |
| 10 μM F primer | 0.8 | SEQ ID NO: 11 |
| 10 μM R primer | 0.8 | SEQ ID NO: 12 |
| Target nucleic acid (54.98 pg/μL) | 0.5 | SEQ ID NO: 13 |
| Sodium cholate | Amount described in Table 20 | DOJINDO LABORATORIES |
| 2-hydroxypropyl-γ-cyclodextrin | Amount described in Table 20 | Wako Pure Chemical Industries, Ltd. |

Finally, the volume of the solution was adjusted with sterile water to 20 μL.

Finally, the volume of each solution was adjusted with sterile water to 20 μL.

TABLE 20

| Sodium cholate concentration (%) | 2-hydroxypropyl-γ-cyclodextrin concentration (%) | Ct value |
|---|---|---|
| 0 | 0 | 21.4 |
| 0 | 8.2 | 21.4 |
| 0.5 | 0 | N.D. |

TABLE 20-continued

| Sodium cholate concentration (%) | 2-hydroxypropyl-γ-cyclodextrin concentration (%) | Ct value |
|---|---|---|
| 1.0 | 0 | N.D. |
| 1.5 | 0 | N.D. |
| 1.5 | 8.2 | 29.9 |

Example 11 Real-Time PCR Using Virus

Recovery from reaction inhibition by sodium cholate and recovery from reaction inhibition by 2-hydroxypropyl-γ-cyclodextrin in real-time PCR were evaluated by the following method using virus.

(1) Of influenza viruses listed in Table 13, 10 μL of type H3N2 (concentration of $10^{5.39}$ $TCID_{50}$/mL) was mixed with 1000 μL of aqueous sodium etiolate solution (concentration of 30.6% (w/w)), thereby preparing a viral extract.

(2) Subsequently, a reagent with the reaction composition described Table 21 was adjusted on a 96-well PCR plate (Applied biosystems) and then sealed with 8 cap strips (applied biosystems).

(3) Next, with the use of Quant Studio 5 (Applied biosystems), after heating at 42° C. for 5 minutes and then heating at 95° C. for 10 seconds, 40 cycles (95° C. for 10 seconds, 60° C. for 34 seconds) of amplification reaction was performed to calculate Ct value. The results are depicted in Table 22.

As a result, it was demonstrated that when a nucleic acid is extracted with sodium cholate from the virus, one-step real-time PCR is inhibited, but the addition of 2-hydroxypropyl-γ-cyclodextrin causes recovery from the reaction inhibition.

It was confirmed by the above results that nucleic acid amplification in the present invention is also applicable to real-time PCR.

TABLE 21

| Reagent | Amount of reagent used (μL) | Purchased from SEQ ID NO: |
|---|---|---|
| 2XOne Step SYBR RT-PCR Buffer 4 | 10 | Takara Bio Inc. |
| PrimeScript. 1step enzyme Mix2 | 0.8 | Takara Bio Inc. |
| ROX Reference Dye II | 0.4 | Takara Bio Inc. |
| 10 μM F primer (for H3N2) | 0.8 | SEQ ID NO: 8 |
| 10 μM R primer (for H3N2) | 0.8 | SEQ ID NO: 11 |
| Viral extract | 1.0 | |
| 2-hydroxypropyl-γ-cyclodextrin | Amount described in Table 22 | Wako Pure Chemical Industries, Ltd. |

Finally, the volume of the solution was adjusted with sterile water to 20 μL. The final concentration of sodium cholate was 1.5%.

Finally, the volume of each solution was adjusted with sterile water to 20 μL. The final concentration of sodium cholate was 1.5%.

TABLE 22

| Sodium cholate concentration (%) | 2-hydroxypropyl-γ-cyclodextrin concentration (%) | Ct value |
|---|---|---|
| 1.5 | 0 | N.D. |
| 1.5 | 8.2 | 21.7 |

The present invention is as described above in detail with reference to specific embodiments. It is obvious for persons skilled in the art that various modifications and changes of the present invention are feasible within the technical idea and the scope of the invention.

Note that the entire contents of Japanese Patent Application No. 2017-047428 filed Mar. 13, 2017, Japanese Patent Application No. 2017-097209 filed May 16, 2017, and Japanese Patent Application No. 2017-215697 filed Nov. 8, 2017 including the Descriptions, Sequence Listings, Claims and Abstracts, are incorporated herein by reference as the disclosure of the Description of the present invention.

The invention claimed is:

1. A kit for extracting and amplifying a nucleic acid of a nucleic acid extraction target from a sample containing the nucleic acid extraction target, comprising (i), (ii) and (iii), wherein the nucleic acid extraction target is selected from microorganisms, animal cells, plant cells, and extracellular vesicles:

(i) a nucleic acid extraction reagent, containing at least a surfactant with a steroid skeleton;
   (ii) γ-cyclodextrin having a C1-4 hydroxyalkyl group, wherein said γ-cyclodextrin having a C1-4 hydroxyalkyl group is 2-hydroxypropyl-γ-cyclodextrin; and
   (iii) a nucleic acid amplification reagent.

2. The kit according to claim 1, wherein the γ-cyclodextrin having a C1-4 hydroxyalkyl group is contained in the nucleic acid amplification reagent.

3. The kit according to claim 1, wherein the concentration of the γ-cyclodextrin having a C1-4 hydroxyalkyl group is 4 or more times the concentration of the surfactant with a steroid skeleton.

4. The kit according to claim 1, wherein the nucleic acid extraction target is a microorganism.

5. A method for extracting and amplifying a nucleic acid of a nucleic acid extraction target from a sample containing the nucleic acid extraction target, comprising (i), (ii) and (iii), wherein the nucleic acid extraction target is selected from microorganisms, animal cells, plant cells, and extracellular vesicles:

(i) extracting the nucleic acid, which involves contacting a sample containing a nucleic acid extraction target with a nucleic acid extraction reagent containing at least a surfactant with a steroid skeleton, thereby obtaining a nucleic acid extract;
   (ii) contacting the nucleic acid extract obtained in (i) with γ-cyclodextrin having a C1-4 hydroxyalkyl group, wherein said γ-cyclodextrin having a C1-4 hydroxyalkyl group is 2-hydroxypropyl-γ-cyclodextrin; and
(iii) amplifying the nucleic acid, which involves contacting the solution obtained in (ii) with a nucleic acid amplification reagent.

6. A method for extracting and amplifying a nucleic acid of a nucleic acid extraction target from a sample containing the nucleic acid extraction target, comprising (i) and (ii), wherein
the nucleic acid extraction target is selected from microorganisms, animal cells, plant cells, and extracellular vesicles:
(i) extracting the nucleic acid, which involves contacting a sample containing the nucleic acid extraction target with a nucleic acid extraction reagent containing at least a surfactant with a steroid skeleton, thereby obtaining a nucleic acid extract; and
(ii) amplifying the nucleic acid, which involves contacting the nucleic acid extract obtained in (i) with a nucleic acid amplification reagent containing γ-cyclodextrin having a C1-4 hydroxyalkyl group, wherein said γ-cyclodextrin having a C1-4 hydroxyalkyl group is 2-hydroxypropyl-γ-cyclodextrin.

7. The method according to claim 5, wherein the nucleic acid extraction target is a microorganism.

8. The method according to claim 6, wherein the nucleic acid extraction target is a microorganism.

9. The kit according to claim 1, wherein the surfactant with a steroid skeleton is at least one selected from the group consisting of cholic acid, taurocholic acid, glycocholic acid, tauroursodeoxycholic, and salts thereof.

10. The method according to claim 5, wherein the surfactant with a steroid skeleton is at least one selected from the group consisting of cholic acid, taurocholic acid, glycocholic acid, tauroursodeoxycholic, and salts thereof.

11. The method according to claim 6, wherein the surfactant with a steroid skeleton is at least one selected from the group consisting of cholic acid, taurocholic acid, glycocholic acid, tauroursodeoxycholic, and salts thereof.

12. The kit according to claim 1, wherein the surfactant with a steroid skeleton is sodium cholate.

13. The method according to claim 5, wherein the surfactant with a steroid skeleton is sodium cholate.

14. The method according to claim 6, wherein the surfactant with a steroid skeleton is sodium cholate.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer 1

<400> SEQUENCE: 1
ttctggaggg gtgaaaatgg                                                   20

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer 2

<400> SEQUENCE: 2
gggtttcgac tttctcttac ttgatcc                                           27

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      T7 Promoter

<400> SEQUENCE: 3
aattctaata cgactcacta tagggaga                                      28

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer 4

<400> SEQUENCE: 4
tttggagagg tgagaatggg                                               20

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer 5

<400> SEQUENCE: 5
gggtttcgac tttctcttac ttgatcc                                       27

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer 6

<400> SEQUENCE: 6
aaactaggaa cgctctgtgc t                                             21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer 7

<400> SEQUENCE: 7
tttgctgtgt tcatagctga gac                                           23

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer 8

<400> SEQUENCE: 8
aattctaata cgactcacta tagggagacc cttacaccat tacactctac              50

```
<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer 9

<400> SEQUENCE: 9
ttaatattga tcaggacatt atcatgtaga                                         30

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer 10

<400> SEQUENCE: 10
tgtgctgttc taattg                                                        16

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      F Primer

<400> SEQUENCE: 11
caggctgcaa taagagatat tttaagct                                           28

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      R Primer

<400> SEQUENCE: 12
gaagtcacac tggtatggtt tctca                                              25

<210> SEQ ID NO 13
<211> LENGTH: 5735
<212> TYPE: DNA
<213> ORGANISM: Artificial Sequence
<220> FEATURE:
<223> OTHER INFORMATION: Description of Artificial Sequence: Synthetic
      target DNA

<400> SEQUENCE: 13
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg        120 ttggcgggtg tcgggctgg cttaactatg cggcatcaga gcagattgta ctgagagtgc        180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagtgccaa gcttgcatgc ctgcaggtcg       420
acatttaggt gacactatag aatacaaagc tgggtaagg agttcaaggc agcgcccaca       480
cccgggggct ctccgcaacc cgaccgcctg tccgctcccc cacttcccgc cctccctccc       540
```

```
acctactcat tcacccaccc acccaccoac ccagagccgg gacggcagcc caggcgcccg    600
ggccccgccg tctcctcgcc gcgatcctgg acttcctctt gctgcaggac ccggcttcca    660
cgtgtgtccc ggagccggcg tctcagcaca cgctccgctc cgggcctggg tgcctacagc    720
agccagagca gcagggagtc cgggacccgg gcggcatctg gccaagtta ggcgccgccg     780 aggccagcgc tgaacgtctc cagggccgga ggagccgcgg ggcgtccggg tctgagccgc    840
agcaaatggg ctccgacgtg cgggacctga acgcgctgct gcccgccgtc ccctccctgg    900
gtggcggcgg cggctgtgcc ctgcctgtga gcggcgcggc gcagtgggcg ccggtgctgg    960
actttgcgcc cccgggcgct tcggcttacg ggtcgttggg cggccccgcg ccgccaccgg   1020
ctccgccgcc accccgccg ccgccgcctc actccttcat caaacaggag ccgagctggg    1080
gcggcgcgga ccgcacgag gagcagtgcc tgagcgcctt cactgtccac ttttccggcc    1140
agttcactgg cacagccgga gcctgtcgct acgggccctt cggtcctcct ccgcccagcc   1200
aggcgtcatc cggccaggcc aggatgtttc ctaacgcgcc ctacctgccc agctgcctcg   1260
agagccagcc cgctattcgc aatcagggtt acagcacggt caccttcgac gggacgccca   1320
gctacggtca cacgccctcg caccatgcgg cgcagttccc caaccactca ttcaagcatg   1380
aggatcccat gggccagcag ggctcgctgg gtgagcagca gtactcggtg ccgcccccgg   1440
tctatggctg ccacaccccc accgacagct gcaccggcag ccaggctttg ctgctgagga   1500
cgccctacag cagtgacaat ttataccaaa tgacatccca gcttgaatgc atgacctgga   1560
atcagatgaa cttaggagcc accttaaagg gagttgctgc tgggagctcc agctcagtga   1620
aatggacaga agggcagagc aaccacagca cagggtacga gagcgataac cacacaacgc   1680
ccatcctctg cggagcccaa tacagaatac acacgcacgg tgtcttcaga ggcattcagg   1740
atgtgcgacg tgtgcctgga gtagccccga ctcttgtacg gtcggcatct gagaccagtg   1800
agaaacgccc cttcatgtgt gcttacccag gctgcaataa gagatatttt aagctgtccc   1860
acttacagat gcacagcagg aagcacactg gtgagaaacc ataccagtgt gacttcaagg   1920
actgtgaacg aaggttttct cgttcagacc agctcaaaag acaccaaagg agacatacag   1980
gtgtgaaacc attccagtgt aaaacttgtc agcgaaagtt ctcccggtcc gaccacctga   2040
agacccacac caggactcat acaggtaaaa caagtgaaaa gcccttcagc tgtcggtggc   2100
caagttgtca gaaaaagttt gcccggtcag atgaattagt ccgccatcac aacatgcatc   2160
agagaaacat gaccaaactc cagctggcgc tttgaggggt ctccctcggg gaccgttcag   2220
tgtcccaggc agcacagtgt gtgaactgct ttcaagtctg actctccact cctcctcact   2280
aaaaaggaaa cttcagttga tcttcttcat ccaacttcca agacaagata ccggtgcttc   2340
tggaaactac caggtgtgcc tggaagagtt ggtctctgcc ctgcctactt ttagttgact   2400
cacaggccct ggagaagcag ctaacaatgt ctggttagtt aaaagcccat tgccatttgg   2460
tgtggatttt ctactgtaag aagagccata gctgatcatg tcccctgac ccttcccttc    2520 tttttttatg ctcgttttcg ctggggatgg aattattgta ccatttcta tcatggaata    2580 tttataggcc agggcatgtg tatgtgtctg ctaatgtaaa ctttgtcatg gtttccattt    2640
actaacagca acagcaagaa ataaatcaga gagcaaggca tcggggggtga atcttgtcta    2700 acattcccga ggtcagccag gctgctaacc tggaaagcag gatgtagttc tgccaggcaa    2760
cttttaaagc tcatgcattt caagcagctg aagaaaaaat cagaactaac cagtacctct    2820
gtatagaaat ctaaaagaat tttaccattc agttaattca atgtgaacac tggcacactg    2880
```

```
ctcttaagaa actatgaaga tctgagattt ttttgtgtat gttttttgact cttttgagtg    2940
gtaatcatat gtgtctttat agatgtacat acctccttgc acaaatggag gggaattcat     3000
tttcatcact gggagtgtcc ttagtgtata aaaaccatgc tggtatatgg cttcaagttg     3060
taaaaatgaa agtgacttta aagaaaata ggggatggtc caggatctcc actgataaga      3120
ctgttttaa gtaacttaag gacctttggg tctacaagta tatgtgaaaa aaatgagact      3180
tactgggtga ggaaatccat tgtttaaaga tggtcgtgtg tgtgtgtgtg tgtgtgtgtg     3240
tgtgtgtgtt gtgttgtgtt ttgttttta agggagggaa tttattattt accgttgctt     3300
gaaattactg tgtaaatata tgtctgataa tgatttgctc tttgacaact aaaattagga    3360
ctgtataagt actagatgca tcactgggtg ttgatcttac aagatattga tgataacact    3420
taaaattgta acctgcattt ttcactttgc tctcaattaa agtctattca atctagagga    3480
tccccgggta ccgagctcga attcgtaatc atggtcatag ctgtttcctg tgtgaaattg    3540
ttatccgctc acaattccac acaacatacg agccggaagc ataaagtgta agcctggg      3600
tgcctaatga gtgagctaac tcacattaat tgcgttgcgc tcactgcccg ctttccagtc    3660
gggaacctg tcgtgccagc tgcattaatg aatcggccaa cgcgcgggga gaggcggttt     3720
gcgtattggg cgctcttccg cttcctcgct cactgactcg ctgcgctcgg tcgttcggct    3780
gcggcgagcg gtatcagctc actcaaaggc ggtaatacgg ttatccacag aatcagggga    3840
taacgcagga aagaacatgt gagcaaaagg ccagcaaaag gccaggaacc gtaaaaaggc    3900
cgcgttgctg gcgtttttcc ataggctccg cccccctgac gagcatcaca aaaatcgacg    3960
ctcaagtcag aggtggcgaa acccgacagg actataaaga taccaggcgt ttccccctgg    4020
aagctccctc gtgcgctctc ctgttccgac cctgccgctt accggatacc tgtccgcctt    4080
tctcccttcg ggaagcgtgg cgctttctca tagctcacgc tgtaggtatc tcagttcggt    4140
gtaggtcgtt cgctccaagc tgggctgtgt gcacgaaccc cccgttcagc ccgaccgctg    4200
cgccttatcc ggtaactatc gtcttgagtc caacccggta agacacgact tatcgccact    4260
ggcagcagcc actggtaaca ggattagcag agcgaggtat gtaggcggtg ctacagagtt    4320
cttgaagtgg tggcctaact acggctacac tagaagaaca gtatttggta tctgcgctct    4380
gctgaagcca gttaccttcg gaaaaagagt tggtagctct tgatccggca acaaaccac     4440
cgctggtagc ggtggttttt ttgtttgcaa gcagcagatt acgcgcagaa aaaaaggatc    4500
tcaagaagat cctttgatct tttctacggg gtctgacgct cagtggaacg aaaactcacg    4560
ttaagggatt ttggtcatga gattatcaaa aaggatcttc acctagatcc ttttaaatta    4620
aaaatgaagt tttaaatcaa tctaaagtat atatgagtaa acttggtctg acagttacca    4680
atgcttaatc agtgaggcac ctatctcagc gatctgtcta tttcgttcat ccatagttgc    4740
ctgactcccc gtcgtgtaga taactacgat acgggagggc ttaccatctg gccccagtgc    4800
tgcaatgata ccgcgagacc cacgctcacc ggctccagat ttatcagcaa taaaccagcc    4860
agccggaagg gccgagcgca gaagtggtcc tgcaacttta tccgcctcca tccagtctat    4920
taattgttgc cgggaagcta gagtaagtag ttcgccagtt aatagtttgc gcaacgttgt    4980
tgccattgct acaggcatcg tggtgtcacg ctcgtcgttt ggtatggctt cattcagctc    5040
cggttcccaa cgatcaaggc gagttacatg atccccatg ttgtgcaaaa aagcggttag     5100
ctccttcggt cctccgatcg ttgtcagaag taagttggcc gcagtgttat cactcatggt    5160
tatggcagca ctgcataatt ctcttactgt catgccatcc gtaagatgct tttctgtgac    5220
tggtgagtac tcaaccaagt cattctgaga atagtgtatg cggcgaccga gttgctcttg    5280
```

```
cccggcgtca atacgggata ataccgcgcc acatagcaga actttaaaag tgctcatcat    5340
tggaaaacgt tcttcggggc gaaaactctc aaggatctta ccgctgttga gatccagttc    5400
gatgtaaccc actcgtgcac ccaactgatc ttcagcatct tttactttca ccagcgtttc    5460
tgggtgagca aaaacaggaa ggcaaaatgc cgcaaaaaag ggaataaggg cgacacggaa    5520
atgttgaata ctcatactct tccttttca atattattga agcatttatc agggttattg     5580
tctcatgagc ggatacatat ttgaatgtat ttagaaaaat aaacaaatag gggttccgcg    5640
cacatttccc cgaaaagtgc cacctgacgt ctaagaaacc attattatca tgacattaac    5700
ctataaaaat aggcgtatca cgaggcccctt tcgtc                              5735

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aattctaata cgactcacta tagggagacc cttacaccat tacactctac                50

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttaatattga tcaggacatt atcatgtaga                                      30

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
tgtgctgttc taattg                                                     16
```